United States Patent [19]
Bair et al.

[11] Patent Number: 6,027,690
[45] Date of Patent: Feb. 22, 2000

[54] KITS FOR DIAGNOSING PRE-MENSTRUAL SYNDROME

[76] Inventors: Glenn O. Bair, 5520 SW. Linconshire Cir., Topeka, Kans. 66614; Austin Shug, 1722 Hummingbird Ct., Marco Island, Fla. 33937

[21] Appl. No.: 09/175,227

[22] Filed: Oct. 20, 1998

Related U.S. Application Data

[62] Division of application No. 08/598,990, Feb. 9, 1996, Pat. No. 5,872,008.

[51] Int. Cl.$^7$ .................................................. G01N 33/48
[52] U.S. Cl. .............................. 422/61; 422/99; 436/63
[58] Field of Search ................ 422/61, 99, 102; 436/63, 65, 56, 57, 111, 128, 129

[56] References Cited

U.S. PATENT DOCUMENTS

| | | | |
|---|---|---|---|
| 4,897,411 | 1/1990 | Giannini | 514/401 |
| 4,946,679 | 8/1990 | Thys-Jacobs | 424/682 |
| 5,093,265 | 3/1992 | Portman et al. | 436/65 |
| 5,266,463 | 11/1993 | Takahashi et al. | 435/26 |
| 5,316,917 | 5/1994 | Roe | 435/15 |
| 5,354,743 | 10/1994 | Thys-Jacobs | 514/167 |
| 5,385,829 | 1/1995 | Takahashi et al. | 435/19 |
| 5,569,457 | 10/1996 | Shug et al. | 424/278.1 |

FOREIGN PATENT DOCUMENTS

WO 89/05979  6/1989  WIPO .

OTHER PUBLICATIONS

Gitten Cederblad et al., "Method for the Determination of Carnitine in the Picomole Range," *Clinica Chimica Acta*, vol. 37, pp. 235–243 (1972).

J. Dennis McGarry et al., "An Improved and Simplified Radioisotope Assay for the Determination of Free and Esterified Carnitine," *Journal of Lipid Research*, vol. 17, pp. 277–280 (1976).

R. Parvin and S. V. Pande, "Microdetermination of (−) Carnitine and Carnitine Acetyltransferases Activity," *Analytical Biochemistry*, vol. 79, pp. 190–201 (1977).

D. F. Horrobin et al., "The Role of Essential Fatty Acids and Prostaglandins in the Premenstrual Syndrome," *The Journal of Reproductive Medicine*, vol. 28, No. 7, pp 465–468 (1983).

D. F. Horrobin et al., "Abnormalities in Plasma Essential Fatty Acid Levels in Women With Premenstrual Syndrome and with Non–malignant Breast Disease," *Journal of Nutritional Medicine*, vol. 2, pp. 259–264 (1991).

P. J. Magill, "Investigation of the Efficacy of Progesterone Pessaries in the Relief of Symptoms of Premenstrual Syndrome," *British Journal of General Practice*, vol. 45, pp. 589–593 (Nov. 1995).

*Primary Examiner*—Randy Gulakowski
*Assistant Examiner*—Alexander Markoff
*Attorney, Agent, or Firm*—Fish & Neave; N. Govindaswamy

[57] ABSTRACT

The present invention provides biochemical assays for diagnosing premenstrual syndrome in human females. A kit for diagnosing premenstrual syndrome in a female human comprising means for determining free and esterified L-carnitine concentration in blood serum or plasma and instructions for employing said means to obtain a ratio of esterified L-carnitine to free L-carnitine. Women who have an esterified to free L-carnitine ratio of greater than about 0.22 and who have a total L-carnitine concentration greater than 20 μmoles/liter are diagnosed as having premenstrual syndrome.

4 Claims, No Drawings

KITS FOR DIAGNOSING PRE-MENSTRUAL SYNDROME

CROSS REFERENCE TO RELATED APPLICATIONS

This application is a divisional of U.S. application Ser. No. 08/598,990, filed Feb. 9, 1996, now U.S. Pat. No. 5,872,008.

TECHNICAL FIELD OF THE INVENTION

The present invention provides biochemical assays for diagnosing premenstrual syndrome in human females. The invention also provides diagnostic kits that utilize these assays.

BACKGROUND OF THE INVENTION

Premenstrual syndrome (PMS) has been defined as a condition characterized by symptoms which recur in the late luteal phase of successive menstrual cycles, but are normally absent during menses and early follicular phase [K. Dalton et al., "PMS: The Essential Guide to Treatment Options; Thorsons, ed., London, England (1994)]. The symptoms associated with PMS range in severity from cravings for sweet or salty foods to headaches and exhaustion to depression, mood swings and irritability.

In its more severe manifestation, women who suffer from PMS are unable to maintain jobs because of their cyclical anger or inability to concentrate caused by the disease. In some individuals, PMS is so severe that it causes suicidal and homicidal feelings that, in some cases, are actually acted upon. It has been estimated that between 20 and 40 percent of menstruating women suffer from PMS symptoms severe enough to interfere with their normal daily activities [D. Rovner et al., *Premenstrual Syndrome*, American Council on Science and Health 1986].

To this day, the medical community is still not universally agreed that PMS is a medical disease. This has led to misdiagnosis and mistreatment of various PMS symptoms as purely psychological disorders. Moreover, certain PMS symptoms may also be observed in other disease states, leading to complications and difficulties in accurate diagnosis.

The biochemical changes responsible for PMS are still uncertain. Progesterone levels have been implicated in the disease, but studies attempting to correlate plasma progesterone levels and PMS have reached contrary conclusions. Some studies suggest that PMS is correlated with higher progesterone levels [K. N. Muse et al., *N. Engl. J. Med*, 311, pp. 591–93 (1984)], others suggest a correlation with lower progesterone levels [K. Dalton, "The Premenstrual Syndrome and Progesterone Therapy", William Heineman, ed., London, England (1984)], still others suggest no correlation at all [M. R. Mundy et al., *Clin. Endocrinology*, 14, pp. 1–9 (1981)]. Despite these disparities, relief of PMS symptoms has been reported after administration of progesterone to PMS patients.

The diagnosis of PMS is somewhat subjective because it is based on the occurrence of cyclical symptoms during the menstrual cycle. The treating physician must rely upon the patient to ascertain the occurrence and cyclicity of such symptoms, usually through the patient's charting of such symptoms on a daily basis for two or three menstrual cycles. Because each patient's analysis of whether or not she is suffering from a given symptom varies, it may be difficult to identify the disease in less severe cases of PMS. Moreover, in the more severe cases of PMS, the patient may be so disabled as to be unable to accurately chart her symptoms or unable to chart the symptoms at all.

Prior art biochemical tests for PMS are known in the art. For example, U.S. Pat. No. 5,093,265 to Portman et al., describes a test for measuring circulating antibodies to luteinizing hormone (LH) to diagnose PMS. M. E. Dalton et al., *Postgraduate Medical Journal*, 57, pp. 560–61, reports a correlation between PMS and sex hormone-binding globulin concentrations in women. Unfortunately, the accuracy and viability of these tests are questionable. Neither has been adopted by the medical community.

Thus, there remains a great need for an accurate biochemical test for the diagnosis of PMS.

SUMMARY OF THE INVENTION

The present invention fills this need by providing accurate biochemical assays for diagnosing PMS and kits which employ them. The assays and kits of this invention measure the ratio of esterified L-carnitine to free L-carnitine in a patient's serum or plasma. Women who have an esterified-:free L-carnitine ratio of greater than about 0.22 are diagnosed as having PMS.

In one aspect, the assays and kits of this invention are designed to confirm or contrast a diagnosis of PMS based upon the occurrence of cyclic symptoms. The assays and kits are also designed to allow physicians to make an initial diagnosis of PMS, without the need to rely upon a patient's charting of her symptoms over a two to three menstrual cycle period. The identification of patients who have PMS even though they exhibit only minor symptoms is important. Such women may potentially experience much more severe symptoms if, for example, they increase the fat in their diet, if they go on a severe calorie-restricted diet or if they begin taking birth control pills or other contraceptive steroids.

DETAILED DESCRIPTION OF THE INVENTION

For the purposes of this invention, a PMS-like symptom is defined as any of the following: cravings for sweet or salty foods; cravings for alcohol; compulsive eating; bloating; diarrhea or constipation; nausea; weight gain or loss; tickling, crawling or prickling on the skin; cold sores; pimples or acne; styes; sinus problems; easy bruising; backache; joint pain or arthritis; overall body aches; cramps; headache; exhaustion; angry outbursts; poor concentration; difficulty in making decisions; insomnia; mood swings; suicidal feelings; crying spells; depression; feelings of worthlessness; easy irritability; feelings of loneliness; frequent accidents or near accidents; panic attacks; breast pain; swelling of fingers, ankles or face; heart palpitations; dizziness; asthma or wheezing; fainting; chest pain; and sensations of tremoring.

In addition, a PMS-like symptom must exhibit cyclic recurrence at similar times, excluding periods of menstrual flow, during two to three consecutive menstrual cycles. In order to determine whether a condition is cyclic, a female should chart each of these conditions every day for at least two consecutive menstrual cycles. In addition, the female should also chart the beginning and end of menstrual flow during these cycles. After charting such conditions through two cycles, both the female and the practitioner can determine whether the occurrence of any particular condition during the next cycle qualifies as a PMS-like symptom.

The present invention provides methods for diagnosing PMS in women by determining the serum or plasma esterified L-carnitine:free L-carnitine ratio. At levels above about 0.22, PMS is indicated.

The basis of this invention is the inventors' hypothesis that a defect in fat metabolism is responsible for the plethora of cyclic symptoms that characterize PMS. More specifically, the inventors believe that PMS is caused by a defect in the translocation of fatty acids into the mitochondria.

Fat is metabolized in the mitochondria of cells. Fatty acids are initially activated outside the mitochondria by thioester linkage to coenzyme A (CoA). The resulting fatty acid-CoA ester then reacts with L-carnitine in a transesterification reaction catalyzed by an outer mitochondrial membrane enzyme, carnitine palmitoyltransferase, producing acyl-carnitine. The acyl carnitine is then translocated across the mitochondrial membrane where it is transesterified with CoA at the inner mitochondrial membrane to regenerate acyl-CoA and free carnitine.

Certain mutations in genes encoding enzymes that play a role, either directly or indirectly, in L-carnitine-mediated translocation of fatty acids can result in a build-up of esterified carnitine, thus increasing the esterified:free L-carnitine ratio. The resulting build-up of unmetabolized fatty acids in the cell alters normal cellular function and causes the physical and mental effects that are characteristic of PMS.

Without being bound by theory, applicants believe that women who suffer from PMS may possess a genetic mutation in the transcription control region of one or more of the genes necessary for fat metabolism. More specifically, applicants believe that this mutation is in a progesterone-responsive enhancer element—a portion of a gene capable of altering transcription levels through the binding of progesterone. This would explain the efficacy of progesterone in alleviating PMS symptoms.

Thus, according to one embodiment, the invention provides a method of diagnosing premenstrual syndrome in a female human comprising the steps of:
  removing an aliquot of blood from said female human on a day when said female human is suffering from at least one PMS-like symptom and isolating the serum or plasma from said blood;
  determining the ratio of esterified L-carnitine to free L-carnitine in said serum or plasma; and
  diagnosing said female human as suffering from premenstrual syndrome if said ratio of esterified L-carnitine to free L-carnitine is greater than about 0.22 and total L-carnitine is greater than 20 μmoles/liter.

In addition, the female human must refrain from taking supplemental L-carnitine for at least fifteen day prior to removing an aliquot of blood for use in this assay. In addition, the female must fast for at least 8 hours prior to removing blood for the assay. Both of these requirements are necessary to insure obtaining accurate concentrations of free and esterified L-carnitine.

In this embodiment, the occurrence of any single PMS-like symptom is sufficient for indicating a day on which ratio of esterified L-carnitine to free L-carnitine may be determined. Preferably, the PMS-like symptom is at least one of the following: cravings for sweet or salty foods; compulsive eating; diarrhea or constipation; weight gain or loss; tickling, crawling or prickling on the skin; cold sores; sinus problems; overall body aches; headache; exhaustion; angry outbursts; mood swings; crying spells; depression; easy irritability; frequent accidents or near accidents; breast pain; and swelling of fingers, ankles or face. More preferably, the female will be suffering from at least three PMS-like symptoms, at least one of which is selected from the above preferred list.

The amount of serum or plasma required for a single assay is about 0.6 ml. Typically, about 5 ml of blood is collected from the patient into a heparin-coated glass tube. Preferably, the blood is collected using a Vacutainer collection device using a standard heparinized collection vessel.

Once removed, the blood or the plasma or serum derived therefrom may be assayed immediately or stored for a period of time prior to performing said assay. Although the blood, serum or plasma may be stored at room temperature for up to 24 hours, it is preferable that it be stored at 4° C. if the assay is not performed immediately after it is obtained from the female. If the blood, plasma or serum will not assayed within 3 days, it is further preferred that it be stored frozen at −20° C. At this temperature, it has a shelf life of approximately 4 weeks and may be assayed at any time during that time frame. Preferably, serum or plasma will be separated from the red blood cells immediately following blood collection. The serum or plasma may then be stored as indicated above or assayed directly.

The determination of the ratio of esterified L-carnitine:free L-carnitine may be achieved by any combination of assays which are capable of determining at least two the following three parameters: free L-carnitine concentration, esterified L-carnitine concentration or total (free+esterified) L-carnitine concentration. The majority of known assays are incapable of measuring esterified L-carnitine concentrations directly in the presence of free L-carnitine. Accordingly, the preferred assays of this invention measure total L-carnitine and free L-carnitine and calculate esterified L-carnitine as the difference between total and free L-carnitine.

In general, the assays for total L-carnitine are merely assay for free L-carnitine preceded by a hydrolysis step that converts any esterified L-carnitine to free L-carnitine. This hydrolysis step is preferably achieved by heating the serum or plasma sample under alkaline pH conditions. Alternatively, hydrolysis may achieved through the use of an acyl-carnitine esterase, such as described in U.S. Pat. No. 5,385,829 to Takahashi et al.

Known assay methods for carnitine which may be employed in this invention fall into several different groups. The first type of assay reacts L-carnitine in a sample with acetyl CoA in the presence of carnitine acetyl transferase (CAT) to produce acetyl-L-carnitine and CoA. The CoA is then reacted with 5,5'-dithio-bis-2-nitrobenzoate (DTNB) to generate thiophenylate ion which is calorimetrically measured. N. Marquis et al., *J. Lipid Res.*, 5, pp. 184–87 (1964); and I. Fritz et al., *J. Biol. Chem.*, 238, pp. 2509–17 (1963). An automated version of this assay is described in U.S. Pat. No. 5,316,917 to Roe.

The second type of assay reacts L-carnitine in a sample with NAD in the presence of L-carnitine dehydrogenase to produce 3-dehydrocarnitine and NADH. The UV absorption of NADH is followed spectrophotometrically to determine L-carnitine concentrations. Z. Fresenius, *Anal. Chem.*, 320, pp. 285–89 (1985); Schopp et al., *Eur. J. Biochem.*, 10, pp. 56–60 (1969); H. Aurich et al., *Eur. J. Biochem.*, 6, pp. 196–201 (1968). A modified version of this assay is also described in U.S. Pat. No. 5,266,463 to Takahashi et al.

The third type of assay is similar to the DTNB method described above, but replaces DNTB with n-[p-(2benzimidazoyl)-phenyl]-malimide (BIPM). The fluorescence of the resulting CoA-BIPM is then measured. K. Watanabe et al., *Ann. Rep. MHW Institute for Nerve Disease*, pp. 315–18 (1986).

The final and most preferred type of assay reacts L-carnitine in a sample with radioactively labeled ($^3$H- or $^{14}$C-) acetyl CoA in the presence of CAT. This produces radiolabelled acetyl-L-carnitine which, after removal of any excess labeled acetyl CoA, is quantitated by measuring radioactivity. M. Hamamoto et al., *J. Japan. Nut. Food Soc.*, 41, pp. 389–95 (1988); R. Parvin et al., *Anal, Biochem.*, 79, pp. 190–201 (1977); J. McGarry et al., *J. Lipid Res.*, 17, pp. 277–81 (1976); G. Cederblad et al., Clin. Chim. Acta, 37, pp. 235–43 (1972).

Known methods of determining concentrations of esterified L-carnitine may also be employed in the assays of this invention, but are less preferred. These methods typically involve hydrolysis of acyl-L-carnitines in a sample followed by quantification of the released fatty acids using chromatography. See U.S. Pat. No. 5,385,829.

According to the most preferred embodiment, free L-carnitine is assayed by reacting a first portion of human female serum with $^{14}$C-acetyl-CoA in the presence of carnitine acetyl transferase and N-ethylmalemide to form $^{14}$C-acetyl-carnitine;

employing means to remove any unreacted $^{14}$C-acetyl-CoA; and determining the amount of $^{14}$C-acetyl-carnitine formed by counting radioactivity and comparing said counts to a standard curve.

Means for removing $^{14}$C-acetyl-CoA without removing $^{14}$C-acetyl-carnitine are known in the art and include the use of activated charcoal or an anion exchange resin. Preferably an anion exchange resin is used. Most preferably, removal is achieved through a column of Dowex anion exchange resin.

Total L-carnitine is preferably assayed by heating a second portion of human female serum, preferably to about 37° C., for 10–30 minute under alkaline pH conditions. Alkaline pH conditions are preferably obtained by treating the serum with 0.5 volumes of 1.5 M KOH. After heat/alkaline treatment, the serum is cooled to room temperature, adjusted to pH 7.6, preferably with $H_3PO_4$, and assayed for free carnitine as described above.

In each assay, the radiolabelled $^{14}$C-acetyl-carnitine is counted using any commercially available scintillation counter. The counts in the sample are then compared to a standard curve derived from known concentrations of free L-carnitine treated under the same assay conditions.

The results of any of these assays may then be used to diagnose PMS. If the total L-carnitine concentration is above 20 $\mu$M and the ratio of esterified: free L-carnitine is above 0.22, the patient is diagnosed as suffering from PMS. Total L-carnitine levels below 20 $\mu$M indicate a carnitine deficiency that would cause skewed esterified:free L-carnitine ratios. This, in turn, would interfere with the accuracy of the diagnosis.

Normal total plasma L-carnitine levels range from 25–79 $\mu$M.

In order to ensure accurate diagnosis, any ratios between 0.20 and 0.25 should be confirmed by repeating the assay on a sample of blood taken on a different day where the female human is suffering from PMS-like symptoms.

This assay is useful to confirm a preliminary diagnosis of PMS based upon the occurrence of PMS-like symptoms. If the female human does not have a ratio above the 0.22 threshold, some other disorder, either physical or mental, is responsible for her PMS-like symptoms.

According to an alternate embodiment of the invention, the assays described above can be used to screen any ovulating human female for PMS. The advantage of this embodiment is that it does not require or rely upon the charting or occurrence of PMS-like symptoms.

In this embodiment, a sample of blood is taken from a female human on any day that she is not experiencing menstrual flow. Again, the woman must have fasted for at least 8 hours prior to the taking of blood. In addition, the female must not have taken any L-carnitine supplements in the past 15 days. The assay is run on serum or plasma isolated from the blood as described above and a ratio of esterified:free L-carnitine is obtained. If the ratio is less than about 0.22, the assay is repeated up to 3 more times at 7 day intervals, unless one of the intervals occurs on a day when the female is experiencing menstrual flow. If one of the intervals should fall on such a day, blood should not be taken until the first day after flow has ceased. If additional assays are needed, the next seven day interval is calculated from the day that blood was actually taken, not from the day when blood was supposed to be taken, but was not because the female was experiencing menstrual flow.

If on any of the four intervals, the ratio of esterified:free L-carnitine is above about 0.22, the woman is diagnosed as suffering from PMS and no additional assays need be performed. If the ratio is below about 0.22 after the four assays, the women is diagnosed as free from PMS.

According to an alternate embodiment, the invention provides another method for using esterified:free L-carnitine ratios to diagnose PMS in an ovulating human female without requiring the charting of PMS-like symptoms. This method comprises the steps of:

determining the length of a human female's menstrual cycle;

removing an aliquot of blood from said human female 5 days prior to the end of a menstrual cycle and isolating the serum or plasma from said blood; and determining the ratio of said esterified L-carnitine to free L-carnitine in said serum or plasma;

If the ratio is less than about 0.22, the assay is repeated every day for up to four more days until said ratio of esterified L-carnitine to free L-carnitine is greater than about 0.22 and said amount of total L-carnitine is greater than 20 $\mu$moles/liter.

If the ratio on any day is greater than about 0.22, the female human is diagnosed as suffering from premenstrual syndrome and need not be tested on subsequent days. If the ratio is less than about 0.22 on all five days (i.e., 5, 4, 3, 2 and 1 day before the end of the menstrual cycle), then the woman is diagnosed as being free from premenstrual syndrome.

The determination of a woman's menstrual cycle length can be made by simply calculating the interval between the beginning of menses in any given cycle and the next recurrence of menses. Many women will, in fact be able to calculate menstrual cycle length based upon their own previous observation. For example, many women routinely record the first day of menses in a calendar book. The length of a woman's menstrual cycle does not vary significantly from one cycle to the next. Therefore, calculations of menstrual cycle length based upon prior observation is sufficient for this assay.

As a practical matter, once the menstrual cycle length is determined, five days prior to the end of the menstrual cycle is determined by counting (menstrual cycle length—5) days after the onset of menses.

The removal of blood and determination of free and esterified L-carnitine for this assay is performed as described above.

As a practical matter, a portion of the blood removed from the female in any of the above-described assays should be subjected to a routine blood work-up, such as that typically performed during an annual physical examination. This will rule out any abnormalities that may cause false positives in this assay. Such abnormalities include severe amino acid deficiencies and vitamin $B_{12}$ deficiency, as well as any conditions which cause severe lactic acidosis.

According to another embodiment, the invention provides a kit for diagnosing PMS in a female human comprising:
  means for determining the concentration of free L-carnitine in blood serum or plasma;
  means for determining the concentration of esterifiea L-carnitine in blood serum or plasma; and
  instructions for using the elements of the kit to obtain a ratio of esterified L-carnitine:free L-carnitine in said serum or plasma and for correlating said ratio to a diagnosis of PMS.

The components of the kit are typically contained within a single package.

Any of the means for determining free and esterified L-carnitine concentrations described above may be employed in the kits of this invention. Preferably the means for determining concentration of free L-carnitine in blood serum or plasma comprise a first container containing a solution of acetyl CoA at a concentration of between 1.2 and 120 mM and a second container containing a solution of DTNB or BIPM at a concentration of between 0.27 to 27 mM at a pH of between about 6.5–8.5. The solutions in the first and second containers are mixed together prior to use to form a solution comprising 0.23 to 23 mM DTNB or BIPM and 0.17 to 17 mM acetyl CoA. More preferably, the means for determining concentration of free L-carnitine additionally comprises a third container containing a solution of carnitine acyl transferase at a concentration of between 1.72 and 172 kU/liter.

The means for determining the concentration of esterified L-carnitine preferably comprises a first container containing a solution of KOH at a concentration of between 1.5 and 5M or an acyl carnitine esterase at a concentration of between 0.1 to 10 kU/liter. This component converts the esterified L-carnitine in the sample to free L-carnitine. The resulting total L-carnitine (free+de-esterified) is then quantified. Esterified L-carnitine is quantified by subtracting free L-carnitine concentration from total L-carnitine concentration.

The instructions included in the kits of this invention are typically on a printed sheet contained within the package or written on the package itself. Of course, the instructions may be included with the kit by other means, such as on a computer readable form (i.e., diskette) in the kit.

The instructions detail the use of the elements of the kit for carrying out the assay and for obtaining a ratio of esterified L-carnitine:free L-carnitine, as well as how to interpret the results in order to diagnose PMS.

According to an alternate embodiment, the kit may additionally comprise any or all of the following: a container containing a solution of L-carnitine at a concentration of between 0.1 and 10 mM for use as a standard; a container containing a solution of octanoyl-L-carnitine at a concentration of between about 0.1 and 10 mM for use as an esterified-L-carnitine control; and a container containing a solution of $H_3PO_4$ or 3-[N-morpholino]propanesulfonic acid in HCl at a concentration of between about 0.1 and 10 M for neutralizing the serum after hydrolysis of esterified L-carnitine in KOH.

In order that the invention described herein may be more fully understood, the following examples are set forth. It should be understood that these examples are for illustrative purposes only and are not to be construed as limiting this invention in any manner.

EXAMPLE 1

Approximately 70 women identified as suffering from PMS-like symptoms on the basis of symptom charting over two to three menstrual periods were used in the initial study. A sample of blood (5 ml) was removed from each of these women on day 21 of their menstrual cycle. (Day 1 is defined as the first day of heavy menstrual flow.) The blood was allowed to clot and we isolated the serum. The serum was stored at 4° C. for 48 hours prior to performing the assay.

The serum was then assayed for free and total L-carnitine concentrations essentially using the $^{14}$C-acetyl CoA method described by R. Parvin et al., *Anal. Biochem.*, 79, pp. 190–201 (1979). The method used differed from the published method in that a Dowex anion exchange column, rather than charcoal, was used to remove unreacted $^{14}$C-acetyl CoA from the sample prior to scintillation counting.

Approximately 90% of the women displayed an esterified L-carnitine:free L-carnitine ratio of greater than 0.22. The results of the assay were then correlated with the presence of PMS-like symptoms on the day the samples were taken. Surprisingly, there was an almost 100% correlation between ratios below 0.22 and the absence of PMS-like symptoms.

This result suggested that women suffering from PMS may display a ratio below the 0.22 threshold on days when they are not experiencing symptoms. Therefore, we decided to take blood samples on a day when a woman was displaying PMS-like symptoms, rather than on a specific day of the menstrual cycle.

EXAMPLE 2

Approximately 40 women identified as suffering from PMS-like symptoms on the basis of symptom charting over two to three menstrual periods were used in the next study. These women had not taken any L-carnitine supplements in the past 15 days. In addition, these women had fasted for at least 8 hours prior to having blood drawn. A sample of blood (5 ml) was removed from each of these women on a day when she was suffering from PMS-like symptoms between day 19 and 25 of their menstrual cycle. The blood was allowed to clot and we isolated the serum. The serum was stored at 4° C. for 48 hours prior to performing the assay. The assay was performed as described in Example 1.

Each of the women had an esterified L-carnitine:free L-carnitine ratio of greater than 0.22. Control women who do not experience any PMS-like symptoms all have ratios of less than 0.22. These results demonstrated that a diagnosis of PMS based upon charting of symptoms can be confirmed by a blood esterified L-carnitine:free L-carnitine ratio of greater than 0.22 on a day when a woman is suffering from such symptoms.

EXAMPLE 3

100 random women are chosen for the next study. These women have not taken any L-carnitine supplements in the past 15 days. In addition, these women have fasted for at least 8 hours prior to having blood drawn. A sample of blood (5 ml) is removed from each of these women on a day when they are not experiencing menstrual flow. The blood is collected by use of a Vacutainer device into a heparin-coated glass vial. The blood is centrifuged and the plasma is isolated. Free and total L-carnitine are measured as described in Example 1. Women who have an esterified:free L-carnitine ratio of greater than 0.22 are diagnosed as having PMS.

Seven days later, a second sample of blood (5 ml) is removed from any women whose esterified:free L-carnitine ratio is below the 0.22 threshold in the first assay. Women who are experiencing menstrual flow at the time of the second 7 day interval are not tested until flow has ceased. Again, plasma is isolated and esterified:free L-carnitine ratios are measured. Women who have an esterified:free L-carnitine ratio of greater than 0.22 in the second assay are diagnosed as having PMS.

Women who are not diagnosed as having PMS in the prior two assays have a third sample of blood removed 7 days after the previous sample, or, if they are experiencing menstrual flow on that day, the first day that flow ceases. Plasma from the blood is assayed in the same manner. Women who have an esterified:free L-carnitine ratio of greater than 0.22 in the third assay are diagnosed as having PMS.

The procedure is repeated a fourth time on any women not diagnosed as having PMS by the three previous assays. Any woman who has an esterified:free L-carnitine ratio of less than 0.22 in all four assays is diagnosed as being free from PMS.

The results of this assay are then confirmed by the PMS-like symptom charting method. Women diagnosed as having PMS by the L-carnitine assay display PMS-like symptoms over a two to three menstrual cycle charting period. Women diagnosed as free from PMS by the L-carnitine assay do not display PMS-like symptoms over a two to three menstrual cycle charting period.

EXAMPLE 4

The menstrual cycle length (M) for each of 100 random women is determined based on the interval between two consecutive onset of menses.

A sample of blood (5 ml) is removed from each of these women on day (M)—5 following the onset of menstrual flow. These women have not taken any L-carnitine supplements in the past 15 days. In addition, these women have fasted for at least 8 hours prior to having blood drawn. The blood is collected by use of a Vacutainer device into a heparin-coated glass vial. The blood is centrifuged and the plasma is isolated. Free and total L-carnitine are measured as described in Example 1. Women who have an esterified-:free L-carnitine ratio of greater than 0.22 are diagnosed as having PMS.

The next day, a second sample of blood (5 ml) is removed from any women whose esterified:free L-carnitine ratio is below the 0.22 threshold in the first assay. Again, plasma is isolated and esterified:free L-carnitine ratios are measured. Women who have an esterified:free L-carnitine ratio of greater than 0.22 in the second assay are diagnosed as having PMS.

Women who are not diagnosed as having PMS in the prior two assays have a third sample of blood removed the following day. Plasma from the blood is assayed in the same manner. Women who have an esterified:free L-carnitine ratio of greater than 0.22 in the third assay are diagnosed as having PMS.

The procedure is repeated the next day on any women not diagnosed as having PHS by the three previous assays. Again, women who have an esterified:free L-carnitine ratio of greater than 0.22 in the third assay are diagnosed as having PMS.

Any woman not diagnosed as having PMS from the previous four assays is subjected to another assay on the next day. Women who have an esterified:free L-carnitine ratio of less than 0.22 in all five assays are diagnosed as being free from PMS.

The results of this assay are then confirmed by the PMS-like symptom charting method. Women diagnosed as having PMS by the L-carnitine assay display PMS-like symptoms over a two to three menstrual cycle charting period. Women diagnosed as free from PMS by the L-carnitine assay do not display PMS-like symptoms over a two to three menstrual cycle charting period.

While I have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A diagnostic kit for diagnosing premenstrual syndrome in a female human who has fasted at least 8 hours and has not taken L-carnitine supplements in the past 15 days, said kit comprising:
   a. means for determining free L-carnitine concentration in blood serum or plasma of said female human;
   b. means for determining total L-carnitine concentration in said blood serum or plasma; and
   c. printed instructions:
      (i) for employing said means for determining said free L-carnitine concentration and said means for determining said total L-carnitine concentration;
      (ii) to obtain esterified L-carnitine concentration by subtracting said free L-carnitine concentration from said total L-carnitine concentration;
      (iii) to obtain a ratio of esterified L-carnitine concentration:free L-carnitine concentration; and
      (iv) for diagnosing said female human as suffering from premenstrual syndrome if said ratio is greater than about 0.22 and said total L-carnitine concentration is greater than 20 $\mu$moles/liter.

2. The kit according to claim 1, wherein said means for determining said free L-carnitine concentration in said blood serum or plasma comprise:
   a. a first container containing a solution of acetyl CoA at a concentration of between 1.2 and 120 mM; and
   b. a second container containing a solution of 5,5-dithiobis-2-nitrobenzoic acid or N-(p-2(-benzimidazolyl)phenyl)maleimide at a concentration of between 0.27 to 27 mM at a pH of between about 6.5–8.5, whereby said solutions in said first and second containers can be mixed prior to use to form a solution comprising 5,5-dithiobis-2-nitrobenzoic acid or N-(4-2(-benzimidazolyl)phenyl)maleimide at a concentration of 0.23 mM to 23 mM and acetyl CoA at a concentration of 0.17 mM to 17 mM.

3. The kit according to claim 2, wherein the means for determining said free L-carnitine concentration additionally comprises a third container containing a solution of carnitine acyl transferase at a concentration of between 1.72 and 172 kU/liter whereby said solution of carnitine acyl transferase in said third container can be mixed with the mixture of said solutions in said first and second containers.

4. The kit according to claim 1, wherein said means for determining said total L-carnitine concentration in said blood serum or plasma comprises a container containing KOH at a concentration of between 1.5 and 5M or an acyl carnitine esterase at a concentration of between 0.1 to 10 kU/liter, whereby said KOH or acyl carnitine esterase can be reacted with said blood serum or plasma.

* * * * *